(12) United States Patent
Brojek et al.

(10) Patent No.: US 7,244,269 B2
(45) Date of Patent: Jul. 17, 2007

(54) METHOD AND THE DEVICE FOR CRYOGENIC THERAPY APPLIED ON THE WHOLE BODY OF A PATIENT

(76) Inventors: Wieslaw Brojek, Al. Prymasa Tysiaclecia 62, PL 01-424 Warsaw (PL); Wlodzimierz Szmurlo, Al. Prymasa Tysiaclecia 62, PL 01-424 Warsaw (PL)

(*) Notice: Subject to any disclaimer, the term of this patent is extended or adjusted under 35 U.S.C. 154(b) by 49 days.

(21) Appl. No.: 10/494,619

(22) PCT Filed: Nov. 5, 2001

(86) PCT No.: PCT/PL01/00087
§ 371 (c)(1),
(2), (4) Date: May 4, 2004

(87) PCT Pub. No.: WO03/039414

PCT Pub. Date: May 15, 2003

(65) Prior Publication Data
US 2005/0004635 A1    Jan. 6, 2005

(51) Int. Cl.
*A61F 7/00* (2006.01)
(52) U.S. Cl. ............................ 607/104; 607/83; 606/20
(58) Field of Classification Search .................. 606/20; 607/83, 87, 104; 62/259.3
See application file for complete search history.

(56) References Cited

U.S. PATENT DOCUMENTS 3,527,414 A    9/1970    Schorsch (Continued)

FOREIGN PATENT DOCUMENTS

DE    3441 094 A1    5/1986

(Continued)

Primary Examiner—Roy D. Gibson
(74) Attorney, Agent, or Firm—Blank Rome LLP

(57) ABSTRACT

Method of carrying out the cryogenic therapy, particularly on the whole body of one or several patient/s, characterized in that said patient/s are introduced along a transport route through the upper part of a chamber and then through the interior of said chamber, wherein said chamber has thermally insulated walls and a space containing a deposited low temperature cooling agent. The patient/s are then led to a cryogenic treatment cabin having a very low temperature from −60.c to −160.c with exposure times ranging from 0.5 to 5 minutes, whereafter said patient/s leave said treatment cabin through the interior of said chamber and further along said transport route outside chamber to an area at room temperature. The corresponding device for carrying out cryogenic therapy is characterized by a chamber with an open upper part and by a separated cryogenic treatment cabin inside said chamber said cabin being cooled in its whole volume by a cooling agent in the form of liquid air sprayed by nozzles. Alternatively, said device for carrying out cryogenic therapy has a cabin cooled by a cooling agent in the form of liquid carbon dioxide or liquid nitrogen sprayed by nozzles, said chamber having an air intake device in its upper part for providing breathing air to said patient/s. Optionally, said device has a chamber having an upper part with a movable cover which is preferably transparent, said chamber comprising illumination means, the cryogenic treatment cabin having an emergency door situated on one side of said of said chamber, said door enabling access for disabled people on wheelchairs, said chamber, said door enabling access for disabled people on wheelchairs, said chamber, also having measuring and control means for temperature and oxygen concentration in order to protect said patient/s.

7 Claims, 3 Drawing Sheets

U.S. PATENT DOCUMENTS 4,838,270 A * 6/1989 Donnerhack et al. ......... 607/83
4,880,003 A * 11/1989 Donnerhack et al. ......... 607/83
5,775,110 A * 7/1998 Waldron .................... 62/50.2

FOREIGN PATENT DOCUMENTS

| DE | 3641293 A1 * | 6/1988 |
| DE | 195 15 287 A1 | 10/1996 |
| DE | 296 15 726 U1 | 11/1997 |
| EP | 0 226 107 A1 | 6/1987 |

* cited by examiner

METHOD AND THE DEVICE FOR CRYOGENIC THERAPY APPLIED ON THE WHOLE BODY OF A PATIENT

FIELD OF THE INVENTION

The subject of the invention is the method and the device for carrying out the cryogenic therapy, particularly on the whole body of the patient, wherein the patient is exposed to the gases cooled to the cryogenic temperature. The process is performed by introducing the patient into the interior of the treatment cabin and exposing the body to the deposition of cold air in the space.

BACKGROUND OF THE INVENTION

There are known methods in the medical technology for performing the cryogenic therapy by exposing some parts of the human body or the whole body to the agents reducing their temperature. It is carried out by using the evaporation of condensed gases or compressed gases. The known devices for carrying out the cryogenic treatment have the therapeutical chamber. The patient, the cryogenic gas loading system, the control system and the protecting system etc are inside the chamber.

There is known from the German Patent Specification no. 3213919 the device for preparating the cryogenic air which is provided to the medical cryogenic chamber. The device has the air compressor, the dryer for removing the steam from the compressed air, the heat exchanger and the condensed gas container. The device is provided with the measuring elements, the control elements and the protective elements. The parts of the device which contain the cryogenic agents are provided with the thermalinsulation. The device requires a long starting time and a stand-by system.

From the Polish Patent Specification no 157168 the device is known for carrying out the cryogenic treatment which has the chamber for patients and the chamber cryogenic air loading unit. The chamber has the loading air circulation system having the air compressor, the dryer and the air cooling circulation system. The cooling air circulation system has the liquid gas vessel and the heat exchangers, wherein it has three heat gas exchangers ie; the preliminary heat exchanger, the main heat exchanger and the final heat exchanger as well as the spraying element. The preliminary heat exchanger and the spraying element are situated inside the chamber for the patients. The device has the favourable operating characteristics displayed in the short starting time and closing time.

The aim of the present invention is to provide the method and the cryogenic device which are directed to carrying out the safe treatment on the whole body of one or several patients.

SUMMARY OF THE INVENTION

The method according to the invention should provide correct and effective treatment, and the device according to the invention should provide the correct supply to the therapeutic chamber wherein the loaded gas has optimal parameters because of the treatment reasons. It should make possible the economical process by taking advantage of the deposition of low temperature gas phenomenon.

The method for carrying out the cryogenic therapy, particularly on the whole body of the patient characterised by that the patient or the patients are introduced along the transport route through the upper part of the chamber, and then through the interior of the chamber wherein the chamber has the thermally insulated walls, and containing the space with the deposited low temperature cooling agent to the cryogenic treatment cabin having very low temperature from $-60$ C. to $-160$ C., where the exposure time ranges from 0,5 to 5 minutes, after words the patient or the patients are led out of the treatment cabin through the interior of the chamber having the space with the deposited low temperature cooling agent then along the transport route outside the chamber to the room temperature area.

The device for carrying out the cryogenic therapy, particularly on the whole body of the patient characterised by that it has a chamber with an open upper part wherein the chamber has thermally insulated walls and containing the space with the deposited low temperature cooling agent and inside the chamber there is the treatment cryogenic cabin separated which is cooled in its whole volume by the cooling agent in the form of the liquid air sprayed by the nozzles.

The modification of the device for carrying out the cryogenic therapy, particularly on the whole body of the patient characterised by that it has a chamber with an open upper part wherein the chamber has thermally insulated walls and containing the space with the deposited low temperature cooling agent and inside the chamber there is the treatment cryogenic cabin separated which is cooled in its whole volume by the cooling agent in the form of the liquid carbon dioxide or liquid nitrogen sprayed by the nozzles wherein the chamber has in the upper part the air intake device which provides the breathing air for the patient or the patients.

The device for carrying out the cryogenic therapy, and its modification according to the invention characterised that the chamber has in the upper part the movable cover which is preferably transparent wherein the chamber has the chamber lighting elements and the cryogenic therapeutic cabin wherein the cabin has the emergency door situated in the side surface of the chamber which enables the access to the disabled people on wheelchairs and the chamber has the measuring and control temperature and oxygen concentration system which protects the patient or the patients.

It is advantageous to perform the cryogenic therapy, particularly on the whole body of the patient according to the present invention because it allows for the correct treatment thanks to the preliminary cooling of the patient's body, which is conducted in the space with the deposited low temperature cooling agent in the chamber, and the next step which is introducing the patient into the treatment cabin. After using the cabin the patient is gradually led out to the normal temperature area through the space with the deposited low temperature cooling agent in the chamber.

It is advantageous to use the device for carrying out the cryogenic therapy, particularly on the whole body of the patient according to the present invention and its modification because it enables high efficiency by reducing the loss of heat while the patient enters and leaves the chamber through the upper part of the chamber and the space with the deposited low temperature cooling agent to the treatment chamber. The reduction of the loss of the heat was obtained by using the movable transparent cover situated above the upper part of the chamber shielding it partially or completely while the patient or the patients are staying inside the cabin and when the cabin is empty. The lighting elements are situated in the internal surfaces of the chamber and allow for the comfortable conditions for the patient and the emergency door situated in the side surface of the chamber enable the direct exit of the patient from the cabin.

BRIEF DESCRIPTION OF THE DRAWINGS

The subject matter of the invention is shown by way of example with the reference to the accompanying drawings wherein.

DETAILED DESCRIPTION OF THE PREFERRED EMBODIMENT

Figure 1:
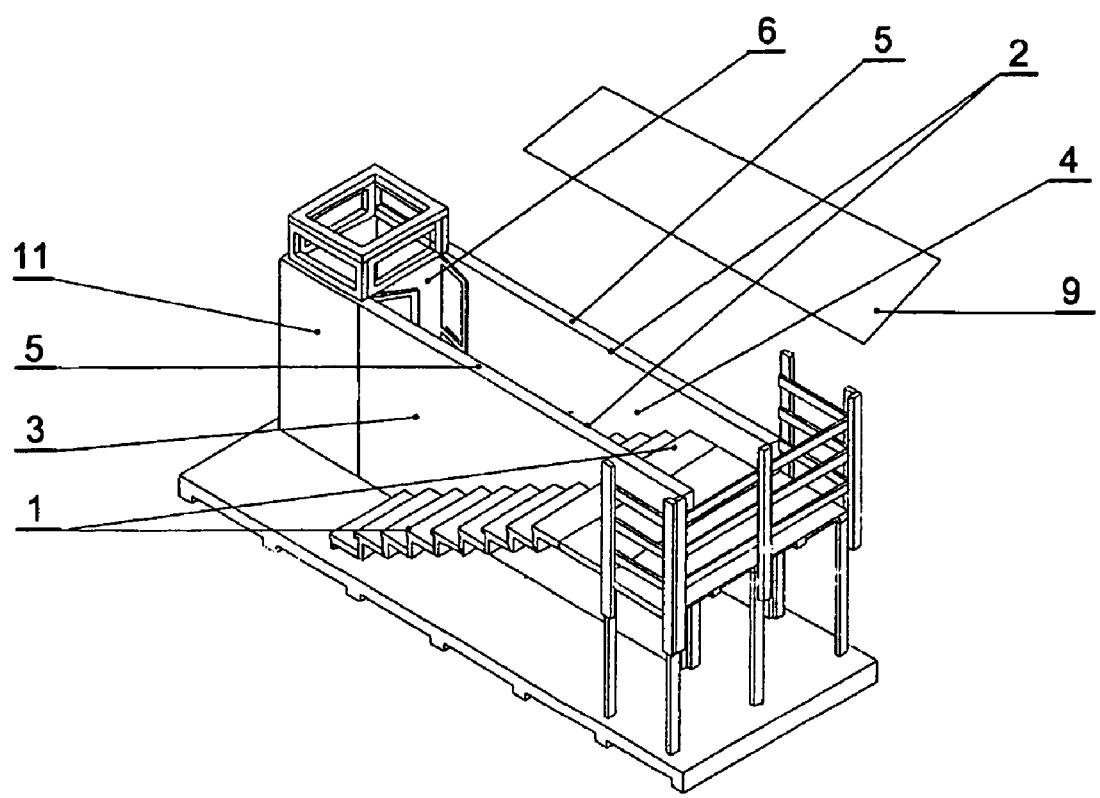
FIG. 1 shows the view of the treatment chamber.
Figure 2:
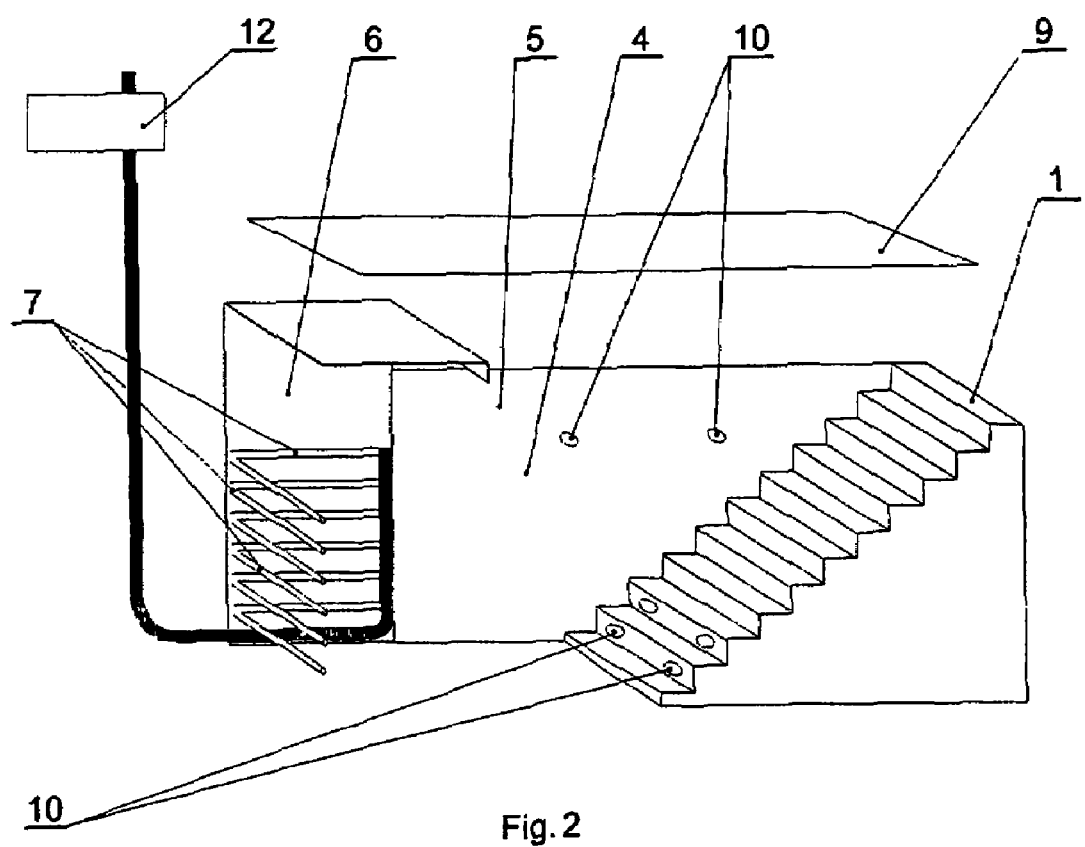
FIG. 2 shows the longitudinal section of the chamber.

The device for carrying out the cryogenic therapy according to the invention which is shown in the FIG. 1 and FIG. 2 has the chamber 3, which is opened in the upper part 2 and the chamber has the thermally insulated walls 5 and the space with the deposited low temperature cooling agent in the form of cold air. At one of the side walls the chamber 3 has the transport route 1 which allows the patient to step down into the interior of the chamber 3 which is the space with the deposited low temperature cooling agent where the agent is in the form of cold air. The patient is preliminarily assimilated to the low temperature and then the patient is introduced into the cryogenic therapeutic cabin 6 with the temperature about −120 C. for the time period of 0,5 to 5 minutes. The exposure time depends on the doctor's recommendations. Next the patient leaves the cryogenic cabin 6 and after passing through the interior of the chamber 3 which is the space with the deposited low temperature cooling agent where the agent is in the form of cold air, the patient is gradually assimilated to the room temperature by leaving the chamber through the transport route 1. The cryogenic therapeutic cabin 6 is situated inside the chamber 3 and is cooled in its whole volume by spraying the cooling agent which is in the form of liquid air by the nozzles 7.

Figure 3:
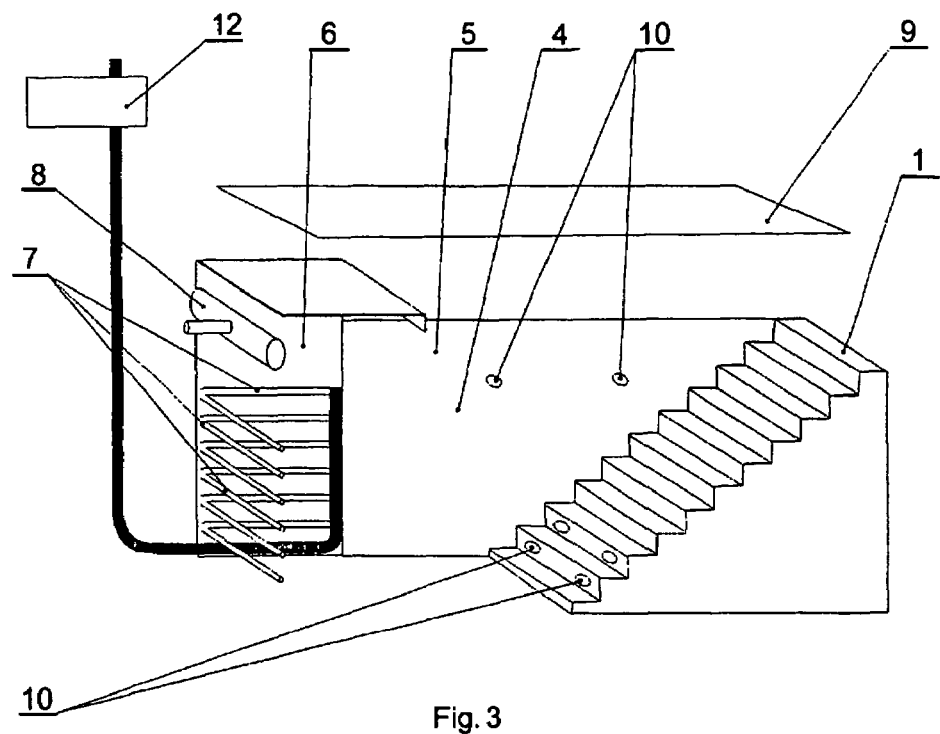
FIG. 3 shows the longitudinal section of the chamber with the air intake device.

The modyfication of the device for carrying out the cryogenic therapy according to the invention is shown in the FIG. 3. has the cryogenic therapeutic cabin 6 situated inside the chamber 3 and the cabin is cooled in the whole volume by spraying the cooling agent wherein the agent is in the form of the liquid carbon dioxide cooled to about −60 C. or in the form of the liquid nitrogen cooled to about −160 C. and the spraying process is carried out by nozzles 7. In the upper part of the cabin 6 is the intake device 8 which provides the breathing air to the patient.

The device for carrying out the cryogenic therapy and its modification have in the upper part 2 of the chamber 3 the transparent movable cover 9, the lighting elements 10, and the cryogenic therapeutic cabin 6 which has the emergency door 11 situated in the side surface of the chamber 3. It allows for the entering of the disabled people using wheelchairs. The device has also measuring and control system 12 for the temperature and the oxygen concentration for safe guarding of the patient or the patients.

The device for the cryogenic therapy could be stationary or mobile adapted to the building conditions.

The invention claimed is:

1. A method for carrying out the cryogenic therapy, particularly on the whole body of a patient, comprising the steps of
    (a) introducing the patient along a transport route through an upper part of a chamber;
    (b) introducing the patient through an interior of the chamber, wherein the chamber has thermally insulated walls and a space containing a low temperature cooling agent;
    (c) introducing the patient to a cryogenic treatment cabin having a temperature from −60° C. to −160° C. and an exposure time of from 0.5 to 5 minutes;
    (d) leading the patient out of the treatment cabin through the interior of the chamber; and
    (e) leading the patient out of the chamber along the transport route to a room temperature area.

2. A device for carrying out the cryogenic therapy, particularly on the whole body of a patient, comprising a chamber having
    an open upper part;
    thermally insulated walls; and
    a treatment cryogenic cabin inside the chamber which is cooled in its whole volume by a cooling agent in the form of the liquid air sprayed by nozzles.

3. The device of claim 2, wherein the chamber has a movable cover in the upper part, lighting elements, and a system for monitoring and controlling temperature and oxygen concentration; and
    wherein the treatment cryogenic cabin has an emergency door situated on a side surface of the chamber which enables access to the cabin by disabled patients on wheelchairs.

4. The device of claim 3, wherein the movable cover is transparent.

5. A device for carrying out the cryogenic therapy, particularly on the whole body of the patient, comprising a chamber having
    an open upper part;
    thermally insulated walls;
    a treatment cryogenic cabin inside the chamber which is cooled in its whole volume by a cooling agent in the form of the liquid carbon dioxide or liquid nitrogen sprayed by nozzles; and
    an air intake device in the upper part which provides breathing air for the patient.

6. The device of claim 5, wherein the chamber has a movable cover in the upper part, lighting elements, and a system for monitoring and controlling temperature and oxygen concentration; and
    wherein the treatment cryogenic cabin has an emergency door situated on a side surface of the chamber which enables access to the cabin by disabled patients on wheelchairs.

7. The device of claim 6, wherein the movable cover is transparent.

* * * * *